United States Patent [19]

Hamada et al.

[11] Patent Number: 5,426,245
[45] Date of Patent: Jun. 20, 1995

[54] PROCESS FOR PRODUCING PHENOLS

[75] Inventors: Michiyuki Hamada, Shinanyo; Hideyuki Niwa, Yokkaichi; Motohiro Oguri, Yokkaichi; Takanori Miyake, Yokkaichi, all of Japan

[73] Assignee: Tosoh Corporation, Yamaguchi, Japan

[21] Appl. No.: 286,504

[22] Filed: Aug. 5, 1994

[30] Foreign Application Priority Data

Aug. 10, 1993 [JP] Japan ................... 5-198297
Oct. 12, 1993 [JP] Japan ................... 5-253973
Nov. 9, 1993 [JP] Japan ................... 5-579356

[51] Int. Cl.⁶ ............... C07C 37/58; C07C 39/04
[52] U.S. Cl. .................................. 568/802
[58] Field of Search ............... 568/800, 802, 801, 771

[56] References Cited

U.S. PATENT DOCUMENTS

| | | | |
|---|---|---|---|
| 3,804,906 | 4/1974 | McAvoy | 568/802 |
| 4,338,471 | 7/1982 | Umemura et al. | 568/802 |

FOREIGN PATENT DOCUMENTS

| | | | |
|---|---|---|---|
| 1483162 | 6/1967 | France | 568/802 |
| 0771078 | 10/1980 | Japan | 568/802 |
| 61-85338 | 4/1986 | Japan | . |
| 5-4935 | 1/1993 | Japan | . |
| 5310622 | 11/1993 | Japan | 568/802 |
| 5310623 | 11/1993 | Japan | 568/802 |

*Primary Examiner*—Werren B. Lone
*Attorney, Agent, or Firm*—Nixon & Vanderhye

[57] ABSTRACT

A phenol is produced by reacting an aromatic compound with oxygen and hydrogen in the liquid phase in the presence of a catalyst comprising a noble metal of group VIII of the periodic table, which is supported on a carrier, and in the co-presence of a vanadium compound. The reaction is carried out either (i) by using as the catalyst a catalyst containing 0% to 0.15% by weight, based on the weight of the catalyst, of halogens, or (ii) further in the co-presence of a diketone compound of the following formula (1) or (2):

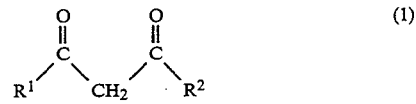

(1)

wherein R¹ and R² independently represents an aryl or alkyl group, which group may have a substituent,

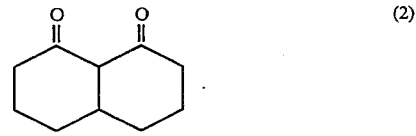
(2)

21 Claims, No Drawings

PROCESS FOR PRODUCING PHENOLS

BACKGROUND OF THE INVENTION

(1) Field of the Invention

This invention relates to a process for producing phenols which are useful as a raw material for a phenol resin, a bisphenol resin, alkyl phenols and aniline and other compounds.

(2) Description of the Related Art

Phenol is the most typical example of phenols having a hydroxyl group in the aromatic ring, and the most typical process for producing phenol is a cumene process. The cumene process has problems in that it comprises many steps such as alkylation, oxidation and decomposition, and acetone is produced undesirably in an amount equimolar to phenol.

As other processes for the production of phenol, there are a Raschig process wherein benzene is chlorinated to chlorobenzene which is converted to phenol, and a toluene-oxidizing process wherein toluene is oxidized to benzoic acid which is converted to phenol. These processes have problems in that the apparatus is liable to corrode, an equipment cost is high because the processes comprise many production steps, and the processes are troublesome because handling of a solid and a slurry is needed.

With regard to polycyclic aromatic compounds having a hydroxyl group in the aromatic ring, a process is industrially established wherein a non-condensed ring compound such as diphenyl or a condensed ring compound such as naphthalene is sulfonated and the sulfonated product is converted to phenylphenol or naphthol, respectively. This process also has a problem such that the apparatus is liable to corrode due to an alkali or an acid.

To solve the problems arising in the above-mentioned processes for producing aromatic compounds having a hydroxyl group, a process has been proposed wherein a corresponding aromatic compound is directly oxidized to an intended phenol. For example, a process for producing phenol which is the most typical example of phenols has been proposed wherein benzene is oxidized at a high temperature of approximately 600° C. or under mild conditions including about room temperature. More specifically, a process has been proposed in Japanese Unexamined Patent Publication No. 56-87527 in which benzene is directly oxidized to phenol in the presence of a catalyst comprising, for example, phosphorus oxide, zinc oxide and silver oxide, or phosphorus oxide, titanium oxide and siver oxide, and in the co-presence of methanol. Further, a process has been proposed in Japanese Unexamined Patent Publication No. 61-85338 in which benzene is reacted with oxygen to produce phenol in the presence of a metal porphyrin, imidazole, platinum and hydrogen.

In the conventional processes for directly oxidizing an aromatic compound to produce a phenol, the conversion of the aromatic compound and the selectivity to the phenol are not highly satisfactory.

SUMMARY OF THE INVENTION

A primary object of the present invention is to provide a process for producing a phenol by a catalytic oxidation of an aromatic compound wherein a high catalytic activity can be maintained for a long reaction time and the intended phenol can be produced with a high selectivity.

In one aspect of the present invention, there is provided a process (hereinafter referred to as "first process") for producing a phenol which comprises reacting an aromatic compound with oxygen and hydrogen in the liquid phase in the presence of a catalyst comprising a noble metal of group VIII of the periodic table, which is supported on a carrier, and in the co-presence of a vanadium compound, characterized in that the catalyst used contains not more than 0.15% by weight of halogens based on the weight of the catalyst.

In another aspect of the present invention, there is provided a process (hereinafter referred to as "second process") for producing a phenol which comprises reacting an aromatic compound with oxygen and hydrogen in the liquid phase in the presence of a catalyst comprising a noble metal of group VIII of the periodic table, which is supported on a carrier, and in the co-presence of a vanadium compound, characterized in that the reaction is carried out further in the co-presence of a diketone compound represented by the following formula (1) or formula (2):

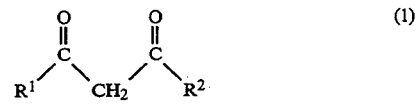

wherein $R^1$ and $R^2$ independently represents an aryl group having 6 to 10 carbon atoms or an alkyl group having 1 to 8 carbon atoms, which group may have a substituent,

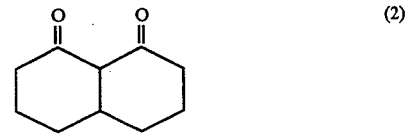

DESCRIPTION OF THE PREFERRED EMBODIMENTS

By the term "phenols" used in this specification and in the appended claims, which are produced by the first and second processes of the present invention, we mean phenol and other monohydric phenols, and polyhydric phenols.

The first and second processes of the present invention will now be described in detail.

In the first and second processes of the present invention, an aromatic compound is reacted with oxygen and hydrogen in the liquid phase in the presence of a catalyst comprising a noble metal of group VIII of the periodic table, supported on a carrier, as well as a vanadium compound. As examples of the noble metal of group VIII of the periodic table, which is supported on a carrier, there can be mentioned ruthenium, rhodium, palladium, iridium and platinum. Of these, rhodium, palladium and platinum are preferable. These metals may be used either alone or as a mixture of at least two thereof. When two noble metals are used in combination, a combination of platinum and palladium is most preferable.

The metal of group VIII of the periodic table is prepared from various inorganic and organic compounds, such as halides, nitrates, sulfates, inorganic complexes and organic acid salts. Taking palladium as an example of the noble metal of group VIII of the periodic table, raw materials for palladium include, for example, inorganic acid salts such as palladium nitrate, palladium chloride and palladium sulfate, inorganic complexes such as tetraammine palladium chloride, and organic acid salts such as palladium acetate. Of these, halogen-free compounds such as palladium nitrate, palladium sulfate and palladium acetate are preferable. Taking platinum as another example of the noble metal, raw materials for platinum include, for example, inorganic complexes such as dinitrodiammineplatinum (II), dichlorodiammineplatinum (II) and tetraamminedichloroplatinum (II), and other platinum compounds such as hexachloroplatinic (VI) acid hexahydrate. Of these, halogen-free compounds such as dinitrodiammineplatinum (II) is preferable.

The procedure, by which the noble metal-containing catalyst used in the first and second processes of the present invention is prepared, is not particularly limited, and the catalyst can be prepared by a conventional procedure which includes, for example, an impregnation, precipitation, kneading, or deposition method. Of these, an impregnation method is most preferable because of ease in preparation of the catalyst.

When the supported catalyst is prepared by the impregnation method, the noble metal-containing raw material is dissolved in a solvent, and a carrier is added in the solution. As examples of the solvent, there can be mentioned water, an aqueous nitric acid solution, an aqueous hydrochloric solution, an aqueous ammonia solution, an aqueous sodium hydroxide solution, acetic acid, benzene, an alcohol and acetone. The solvent is removed by a conventional procedure and the noble metal-containing raw material, supported on a carrier, is reduced to a metallic state either directly or after calcination. Where the noble metal-containing raw material is calcined, the calcination method is not particularly limited, and the calcination is usually carried out at a temperature of 200° to 1,000° C. in an oxygen-containing gaseous atmosphere or an inert gas atmosphere. When a catalyst comprising two or more noble metals of group VIII of the periodic table, supported on a carrier, is prepared, the noble two or more metals (e.g., platinum and palladium) may be supported simultaneously or in succession on the carrier.

In the first process of the present invention, the catalyst used does not contain or contains not more than 0.15% by weight, preferably not more than 0.10% by weight, of halogens based on the weight of the catalyst. The term "halogens" used herein means chlorine, bromine and iodine. If the content of halogens in the catalyst is more than 0.15% by weight, the catalyst activity is insufficient for the intended activity. The catalyst which does not contain or contains up to 0.15% by weight of halogens is prepared either by a process wherein a halogen-free noble metal material and a halogen-free carrier are used, or, even when a halogen-containing noble metal material or a halogen-containing carrier are used, by a process wherein the calcination is effected in the process for preparing the catalyst to an extent such that the halogen content is reduced to a level not more than 0.15% by weight, or wherein, after calcination or reduction, the catalyst or the catalyst precursor is washed with a wash liquid to remove halogens so that the halogen content is reduced to a level not more than 0.15% by weight. The washing for removing halogens is carried out by, for example, decantation, centrifugal separation or filtration. As examples of the wash liquid, there can be mentioned water and a basic liquid such as an aqueous solution of ammonia, sodium hydroxide, potassium hydroxide, calcium hydroxide or barium hydroxide.

In the first and second processes of the present invention, the noble metal of group VIII of the periodic table, supported on a carrier, must be in a metallic state during the process for producing a phenol. For this purpose, the noble metal-containing raw material supported on a carrier is subjected to a reduction treatment before the use of the noble metal-containing catalyst for the phenol-producing reaction. The reduction treatment can be carried out either in the process for preparing the catalyst or in the reaction system for producing a phenol. The manner in which the reduction treatment is carried out is not particularly limited, and there are usually adopted a wet reduction method wherein a solution of a reducing agent such as sodium formate, formaldehyde or hydrazine is used, or a dry reduction method wherein reduction is conducted in the gas phase by using a reducing gas such as hydrogen or carbon monoxide, which is diluted with an inert gas such as nitrogen or helium. The temperature at which the reduction treatment is conducted is not particularly limited, provided that the raw material of the noble metal of group VIII of the periodic table is reduced to a metallic state. Usually the temperature employed is in the range of 0° to 200° C. in the wet reduction method and in the range of 0° to 500° C. in the dry reduction method.

The amount of the noble metal supported on a carrier is usually in the range of 0.01 to 20% by weight, preferably 0.1 to 10% by weight, as metal, based on the total weight of the noble metal and the carrier. When two or more noble metals such as platinum and palladium are used, the total amount of the noble metals should fall within the above-mentioned range. If the amount of the noble metal is larger than 20% by weight, the rate of reaction becomes large but the production cost increases because the noble metal is expensive. If the amount of the noble metal is smaller than 0.01% by weight, the rate of reaction is very slow and the production process is not advantageous from an industrial viewpoint.

In the case where two or more noble metals are used in combination, the catalyst performance varies depending upon the particular proportion of the noble metals, and therefore, the proportion should be selected so that the optimum result can be obtained. For example, when both platinum and palladium are supported, the proportion of palladium to platinum is selected within the range of 0.01 to 100, preferably 0.1 to 10, as the atomic ratio of palladium/platinum.

The carrier used in the first and second processes of the present invention is not particularly limited and any conventional carriers can be used. As specific examples of the carrier, there can be mentioned silica, alumina, titania, zirconia and binary oxides thereof; zeolites; carbonaceous materials such as coconut shell active carbon; and base metal oxides and binary oxides containing a base metal oxide such as divanadyl pyrophosphate. Of these, zirconia and titania are preferable.

The suitable amount of the catalyst used in the present invention greatly varies depending upon the particular type of reaction, and, for example, when the reaction is carried out by a method wherein a reactant is continuously passed through a fixed bed, the suitable amount varies depending upon the rate of reaction and the heat balance. Thus, it is difficult to indiscriminately define the numerical range for the suitable amount of the catalyst. When the reaction is carried out in a suspension bed in a batchwise or semi-batchwise manner or by a continuously passing procedure, the amount of the catalyst is usually 0.01 to 30% by weight, preferably 0.05 to 20% by weight, based on the weight of the reaction mixture. If the amount of the catalyst used in the suspension bed is too large, it becomes occasionally difficult to stir the reaction solution.

The vanadium compound and the catalyst may be incorporated separately in the reaction system. When the vanadium compound is incorporated separately from the catalyst, the vanadium compound is preferably in the state of dissolved in the reaction system. For example, the vanadium compound is dissolved in a solvent or a reactant material and the solution is supplied to the reaction mixture, or the vanadium compound is suspended in the reaction mixture so that the vanadium compound is gradually dissolved in the reaction mixture.

As specific examples of the vanadium compound, there can be mentioned oxides such as vanadium pentoxide and vanadium trioxide, halides such as vanadium trichloride, vanadium oxydichloride and vanadium oxytrichloride, sulfates such as vanadyl sulfate, organic acid salts such as vanadyl oxalate and vanadium oxide stearate, ammonium salts such as ammonium metavanadate, and organic complex salts such as vanadium (III) acetylacetonate and vanadium oxide acetylacetonate. Of these, vanadium (III) acetylacetonate and vanadium oxide acetylacetonate, which are free from halogens, are preferable.

The concentration of the vanadium compound present in the reaction system varies depending upon the particular type of reaction, but is usually in the range of 0.5 ppm to 5% by weight, preferably 1 ppm to 1% by weight. If the vanadium concentration is too small, it is possible that an acceptable rate of reaction cannot be obtained. In contrast, if the vanadium concentration exceeds 5% by weight, the reaction activity does not increase and the production cost of the phenol increases.

It is possible that the vanadium compound present in the reaction system is in the state of supported on a carrier on which the noble metal is also supported. As the vanadium compound supported on the carrier, vanadium pentoxide is preferable. The amount of vanadium pentoxide supported on the carrier is usually in the range of 0.1 to 99% by weight, preferably 3 to 20% by weight, based on the total weight of the catalyst. As raw materials used for the preparation of vanadium pentoxide, there can be mentioned, for example, halides such as vanadium trichloride, vanadium oxydichloride and vanadium oxytrichloride, sulfates such as vanadyl sulfate, organic acid salts such as vanadyl oxalate and vanadium oxide stearate, ammonium salts such as ammonium metavanadate, and organic complex salts such as vanadium (III) acetylacetonate and vanadium oxide acetylacetonate. Of these, vanadium (III) acetylacetonate and vanadium oxide acetylacetonate, which are free from halogens, are preferable.

The vanadium-containing raw material can be supported on a carrier by a conventional method as in the case where the noble metal-containing raw material is supported on the carrier. After the vanadium-containing raw material is supported on the carrier, the raw material is heated to be converted to vanadium pentoxide. The procedure by which the raw material is heated is not particularly limited provided that vanadium pentoxide is finally produced. Usually the heating is carried out at a temperature of 200° to 1,000° C. under a stream of an oxygen-containing gas or another oxidative gas, or in the absence of an oxygen-containing gas. The order in which the vanadium-containing raw material and the noble metal-containing raw material are supported on the carrier is not particularly limited. The two raw materials may be incorporated with the carrier either in any order or simultaneously. To obtain a good reproducibility, it is preferable that the vanadium-containing raw material is first supported on a carrier and is heated to be oxidized, and the noble metal-containing raw material is then supported on the vanadium pentoxide-supported carrier and is reduced to the noble metal.

In the second process of the present invention, a diketone compound represented by the above formula (1) or (2) is made present in the reaction system, in addition to the noble metal catalyst and the vanadium compound. As specific examples of the diketone compound, there can be mentioned acetylacetone, propionylacetone, butyrylacetone, isobutyrylacetone, caproylacetone, trifluoroacetylacetone, thenoyltrifluoroacetone, benzoylacetone, dibenzoylmethane and decalin-1,8-dion. These diketones may be used either alone or as a mixture of two or more thereof. Of these, acetylacetone is most preferable because of ease in availability and good chemical stability.

The amount of the diketone compound present in the reaction system is preferably in the range of 0.01 to 1.5 equivalent, more preferably 0.05 to 1.2 equivalent, per gram atom of vanadium. If the amount of the diketone compound is smaller than 0.01 equivalent, the intended high selectivity to a phenol and good maintenance of high catalyst activity become difficult to obtain. In contrast, if the amount of the diketone compound is larger than 1.5 equivalent, the rate of reaction is occasionally lowered.

The manner in which the ketone compound is incorporated in the reaction system is not particularly limited. For example, the diketone compound is dissolved in a solvent or a starting reactant material and the solution is incorporated in the reaction system, or the diketone compound is incorporated dividedly in small doses.

The content of halogens in the catalyst used in the second process of the present invention is preferably not larger than 0.15% by weight, more preferably not larger than 0.10% by weight, based on the weight of the catalyst.

The aromatic compound used as a starting material in the first and second processes of the present invention has at least one condensed or non-condensed aromatic ring and may have a substituent such as, for example, an alkyl group or a hydroxyl group. As specific examples of the aromatic compound, there can be mentioned monocyclic aromatic compounds having 6 to 12 carbon atoms, preferably 6 to 10 carbon atoms, such as benzene, toluene, xylene, cumene, anisole and benzoic acid, non-condensed polycyclic aromatic compounds having 2 to 4 aromatic rings, preferably 2 aromatic rings, such as diphenyl, diphenylmethane and diphenyl ether, and condensed polycyclic aromatic compounds having 2 to 4 rings, preferably 2 rings, such as naphthalene and indene.

The reaction in the processes of the present invention is carried out in the liquid phase wherein, if desired, a solvent is used. The solvent used may be either the starting aromatic compound per se or another appropriate solvent. As the solvent, organic solvents are usually used. As specific examples of the organic solvent, there can be mentioned saturated hydrocarbons such as pentane and cyclohexane, nitriles such as acetonitrile, ethers such as methyl ether and ethyl ether, ketones such as acetone and methyl ethyl ketone, esters such as ethyl acetate and butyl acetate, amides such as acetamide and N,N'-dimethylacetamide, and organic acids such as formic acid, acetic acid and propionic acid. These solvents may be used either alone or in combination. Water also may be used as the solvent either alone or as a mixture thereof with an organic solvent.

If desired, an inorganic acid can be added to the organic solvent. As the inorganic acid, there can be mentioned, for example, phosphoric acid, sulfuric acid and nitric acid. When an inorganic acid is added, the amount of the inorganic acid should be such that the concentration thereof is not more than 0.5 N so as to prevent dissolution of the catalyst components and corrosion of the apparatus.

The amount of the solvent is not particularly limited. However, if the amount of the solvent is too large, the rate of reaction is lowered, and therefore, the amount of the solvent other than the starting aromatic compound is in the range of 1 to 60% by weight based on the weight of the total reaction mixture.

The oxygen and hydrogen gases used in the present invention may be diluted with an inert gas such as nitrogen, helium, argon or carbon dioxide. As the oxygen, air may be used. The oxygen and hydrogen gases are supplied to the reaction system for the reaction with an aromatic compound by a procedure wherein a mixture of oxygen and hydrogen is supplied to the reaction system or a procedure wherein an oxygen-containing gas and a hydrogen-containing gas are alternately supplied to the reaction system.

The suitable amount of oxygen varies depending upon the particular reaction procedure and reaction conditions, but is usually in the range of 0.01 ml/min to 1,000 ml/min per gram of the catalyst. If the amount of oxygen is smaller than 0.01 ml/min, the productivity is undesirably low. If the amount of oxygen is larger than 1,000 ml/min, the conversion of oxygen is reduced and the process is not advantageous from an industrial viewpoint. The proportion of oxygen to hydrogen is not particularly limited and can be arbitrarily varied, but the $H_2/O_2$ ratio is preferably in the range of 0.1 to 10 by mole.

The reaction temperature and pressure are not particularly limited provided that the reaction takes place in the liquid phase. When a high reaction temperature is employed for enhancing the rate of reaction, the reaction may be carried out under a high pressure. A practically acceptable reaction temperature is in the range of room temperature to 200° C. When the reaction temperature is lower than room temperature, the conversion of the aromatic compound is very low. When the reaction temperature exceeds 200° C., the selectivity to the intended phenol is occasionally reduced. Usually the reaction pressure is in the range of normal pressure to 200 kg/cm², preferably normal pressure to 50 kg/cm².

The procedure for effecting the reaction is not particularly limited, and there are adopted a batchwise procedure wherein a starting aromatic compound, a noble metal catalyst, a vanadium compound, oxygen, hydrogen and an optional solvent are charged together simultaneously in a reactor; a procedure wherein semi-batchwise procedure wherein oxygen and/or hydrogen are continuously blown into a reactor having been charged with the other ingredients; and a continuous procedure using a fixed bed or a suspension bed wherein an aromatic compound, oxygen and hydrogen are continuously supplied to a reactor while unreacted gas and the liquid reaction mixture are continuously withdrawn therefrom.

When the aromatic compound is continuously supplied, the feed rate of the aromatic compound is usually from $1 \times 10^{-5}$ g/min to $1 \times 10^2$ g/min, per gram of the catalyst. If the feed rate is smaller than $1 \times 10^{-5}$ g/min, the productivity is very low. If the feed rate is larger than $1 \times 10^2$ g/min, the amount of the unreacted aromatic compound is occasionally large, and the process is not advantageous from an economical viewpoint.

The invention will now be described more specifically by the following examples that by no means limit the scope of the invention. In the examples % is by weight unless otherwise specified.

The content of halogens in the catalyst was determined as follows. Namely, 30 mg of a catalyst and 10 mg of calcium carbonate (internal standard) were incorporated with 60 mg of starch, and the mixture was press-molded by a press-molding apparatus to obtain a disc-form sample. Using an X-ray fluorescent spectrophotometer VF-320A of Shimadzu Corp., the intensity of X-ray fluorescence for chlorine (spectral crystal: Ge (111), Kα ray: $2\theta=92.76$ deg.) and the intensity of X-ray fluorescence for calcium (spectral crystal: Ge (111), Kα ray: $2\theta=61.90$ deg.) were measured. The ratio of the X-ray fluorescent intensity for chlorine to that for calcium was calculated, and the content of chlorine in the catalyst was determined from a calibration curve of a known substance. Similarly, the intensity of X-ray fluorescence for bromine (spectral crystal: LiF (220), Kα ray: $2\theta=42.90$ deg.) and the intensity of X-ray luminescence for iodine (spectral crystal: LiF (220), Kα ray: $2\theta=17.60$ deg.) were measured and the contents of bromine and iodine in the catalyst were determined.

EXAMPLE 1

With 6.0 ml of distilled water, 165 mg of a solution of dinitroammineplatinum in aqueous nitric acid, containing 4.591% of platinum, was incorporated, and 1.50 g of zirconia having a specific surface area of 98 m²/g and a particle diameter of not larger than 200 mesh, supplied by Norton Co., was then added to the aqueous solution. The mixture was evaporated to dryness on a hot water bath and the dry product was reduced in a stream of a gaseous 10% hydrogen/-90% nitrogen mixture at 250° C. for one hour to prepare a 0.5% Pt/zirconia catalyst (hereinafter abbreviated to "PT-1"). The X-ray fluorescent analysis revealed that chlorine, bromine and iodine were not detected in PT-1.

A glass reactor having a 100 ml volume and equipped with a reflux condenser was charged with 20 ml of benzene, 25 ml of acetic acid and 6.1 mg of vanadium (III) acetylacetonate, and 0.10 g of the 0.5% Pt/zirconia catalyst (PT-1) was added to the charge. The content of the reactor was heated to 60° C., and, while the heated content was stirred by a magnetic stirrer, hydrogen was supplied at a rate of 40 ml/min to the content for 30 minutes to pretreat the catalyst, and then hydrogen and air were simultaneously supplied to the content at rates of 24 ml/min and 38 ml/min, respectively, to effect oxidation of benzene. When one hour elapsed after the commencement of reaction, the product in the liquid reaction mixture was analyzed by gas chromatography. The results are shown in Table 1.

EXAMPLE 2

In 12.1 ml of distilled water, 28.3 mg of tetraaminedichloroplatinum 1.04 hydrate was dissolved, and 3.12 g of zirconia having a specific surface area of 98 $m^2/g$ and a particle diameter of not larger than 200 mesh, supplied by Norton Co., was then added to the aqueous solution. The mixture was evaporated to dryness on a hot water bath and the dry product was reduced in a stream of a gaseous 10% hydrogen/90% nitrogen mixture at 250° C. for one hour. Thus-obtained powder was suspended in 100 ml of distilled water. The mixture was stirred thoroughly at 20° C. and then filtered. This washing treatment was repeated five times. Under a nitrogen stream, the finally fitered material was dried at 110° C. for one hour. The dried product was reduced in a stream of 10% $H_2$/90% $N_2$ mixture at 250° C. for one hour to prepare a 0.5% Pt/zirconia catalyst (hereinafter abbreviated to "PT-2"). The X-ray fluorescent analysis revealed that the content of chlorine in PT-2 was 0.05% and bromine and iodine were not detected in PT-2.

Oxidation of benzene was carried out by the same procedure as that employed in Example 1 except that PT-2 was used instead of PT-1 as the catalyst. The results are shown in Table 1.

COMPARATIVE EXAMPLE 1

In 8.8 ml of distilled water, 20.7 mg of tetraaminedichloroplatinum 1.04 hydrate was dissolved, and 2.28 g of zirconia having a specific surface area of 98 $m^2/g$ and a particle diameter of not larger than 200 mesh, supplied by Norton Co., was then added to the aqueous solution. The mixture was evaporated to dryness on a hot water bath and the dry product was reduced in a stream of a gaseous 10% hydrogen/90% nitrogen mixture at 250° C. for one hour to prepare a 0.5% Pt/zirconia catalyst (hereinafter abbreviated to "PT-3"). The X-ray fluorescent analysis revealed that the content of chlorine in PT-3 was 0.16% and bromine and iodine were not detected in PT-3.

Oxidation of benzene was carried out by the same procedure as that employed in Example 1 except that PT-3 was used instead of PT-1 as the catalyst. The results are shown in Table 1.

COMPARATIVE EXAMPLE 2

In 4.0 ml of distilled water, 14.5 mg of hexachloroplatinic (IV) acid hexahydrate was dissolved, and 1.14 g of zirconia having a specific surface area of 98 $m^2/g$ and a particle diameter of not larger than 200 mesh, supplied by Norton Co., was then added to the aqueous solution. The mixture was evaporated to dryness on a hot water bath and the dry product was reduced in a stream of a gaseous 10% hydrogen/90% nitrogen mixture at 250° C. for one hour to prepare a 0.5% Pt/zirconia catalyst (hereinafter abbreviated to "PT-4"). The X-ray fluorescent analysis revealed that the content of chlorine in PT-4 was 0.41% by weight and bromine and iodine were not detected in PT-4.

Oxidation of benzene was carried out by the same procedure as that employed in Example 1 except that PT-4 was used instead of PT-1 as the catalyst. The results are shown in Table 1.

EXAMPLE 3

In 6.25 g of ethanol, 19.5 mg of rhodium (III) acetylacetonate was dissolved, and 1.00 g of zirconia having a specific surface area of 104 $m^2/g$ and a particle diameter of not larger than 200 mesh, supplied by Norton Co., was then added to the solution. The mixture was dried at a reduced pressure by using a rotary evaporator and the dry product was reduced in a stream of a gaseous 10% hydrogen/-90% nitrogen mixture at 350° C. for one hour to prepare a 0.5% Rh/zirconia catalyst (hereinafter abbreviated to "RH-1"). The X-ray fluorescent analysis revealed that chlorine, bromine and iodine were not detected in RH-1.

Oxidation of benzene was carried out by the same procedure as that employed in Example 1 except that RH-1 was used instead of PT-1 as the catalyst. The results are shown in Table 1.

COMPARATIVE EXAMPLE 3

In 4.0 ml of distilled water, 12.6 mg of rhodium chloride trihydrate was dissolved, and 1.00 g of zirconia having a specific surface area of 98 $m^2/g$ and a particle diameter of not larger than 200 mesh, supplied by Norton Co., was then added to the aqueous solution. The mixture was evaporated to dryness on a hot water bath, and the dry product was reduced in a stream of a gaseous 10% hydrogen/-90% nitrogen mixture at 250° C. for one hour to prepare a 0.5% Rh/zirconia catalyst (hereinafter abbreviated to "RH-2"). The X-ray fluorescent analysis revealed that the content of chlorine in RH-2 was 0.80%, and bromine and iodine were not detected in RH-2.

Oxidation of benzene was carried out by the same procedure as that employed in Example 1 except that RH-2 was used instead of PT-1 as the catalyst. The results are shown in Table 1.

EXAMPLE 4

With 4.0 ml of distilled water, 121 mg of an aqueous palladium nitrate solution containing 4.414% of palladium was incorporated, and zirconia having a surface area of 104 $m^2/g$ and a particle diameter of not larger than 200 mesh, supplied by Norton Co., was then added to the mixture. The mixture was dried at a reduced pressure by using a rotary evaporator and the dry product was reduced in a stream of a gaseous 10% hydrogen/90% nitrogen mixture at 250° C. for one hour to prepare a 0.5% Pd/zirconia catalyst (hereinafter abbreviated to "PD-1"). The X-ray fluorescent analysis revealed that chlorine, bromine and iodine were not detected in PD-1.

Oxidation of benzene was carried out by the same procedure as that employed in Example 1 except that PD-1 was used instead of PT-1 as the catalyst. The results are shown in Table 1.

EXAMPLE 5

In 4.0 ml of acetone, 10.5 mg of palladium acetate was dissolved, and 1.00 g of zirconia having a specific surface area of 104 $m^2/g$ and a particle diameter of not larger than 200 mesh, supplied by Norton Co., was then added to the solution. The mixture was dried at a reduced pressure by using a rotary evaporator and the dry product was reduced in a stream of a gaseous 10% hydrogen/90% nitrogen mixture at 250° C. for one hour to prepare a 0.5% Pd-/zirconia catalyst (hereinafter abbreviated to "PD-2"). The X-ray fluorescent analysis revealed that chlorine, bromine and iodine were not detected in PD-2.

Oxidation of benzene was carried out by the same procedure as that employed in Example 1 except that PD-2 was used instead of PT-1 as the catalyst. The results are shown in Table 1.

COMPARATIVE EXAMPLE 4

In 4.0 ml of distilled water, 12.3 mg of tetraaminedichloropalladium 0.70 hydrate was dissolved, and 1.00 g of zirconia having a specific surface area of 98 $m^2/g$ and a particle diameter of not larger than 200 mesh, supplied by Norton Co., was then added to the aqueous solution. The mixture was evaporated to dryness on a hot water bath, and the dry product was reduced in a stream of a gaseous 10% hydrogen/90% nitrogen mixture at 250° C. for one hour to prepare a 0.5% Pd/zirconia catalyst (hereinafter abbreviated to "PD-3"). The X-ray fluorescent analysis revealed that the content of chlorine in PD-3 was 0.35%, and bromine and iodine in PD-3.

Oxidation of benzene was carried out by the same procedure as that employed in Example 1 except that PD-3 was used instead of PT-1 as the catalyst. The results are shown in Table 1.

tor was heated to 60° C., and, while the heated content was stirred by a magnetic stirrer, hydrogen was supplied at a rate of 40 ml/min to the content for 30 minutes to pretreat the catalyst, and then hydrogen and air were simultaneously supplied to the content at rates of 24 ml/min and 38 ml/min, respectively, to effect oxidation of benzene. When one hour elapsed after the commencement of reaction, the product in the liquid reaction mixture was analyzed by gas chromatography. The results are shown in Table 2.

EXAMPLE 7

With 4.0 ml of distilled water, 109 mg of a dinitrodiammineplatinum solution in nitric acid, containing 4.59% of platinum, and 6.0 mg of an aqueous palladium nitrate solution containing 4.41% of palladium were incorporated, and 1.00 g of zirconia having a specific surface area of 104 $m^2/g$ and a particle diameter of not larger than 200 mesh, supplied by Norton Co., was then added to the solution. The mixture was dried at a reduced pressure by using a rotary evaporator and the dry product was reduced in a stream of a gaseous 10% hydrogen/90% nitrogen mixture at 250° C. for one hour to prepare a 0.50% Pt-0.027% Pd/zirconia catalyst

TABLE 1

| Example No. | Catalyst | Starting noble metal salt | Washing *1 | Halogen content (% by weight) | | | Rate of production (m-mol/hr) | |
|---|---|---|---|---|---|---|---|---|
| | | | | Cl | Br | I | Phenol | Benzoquinone |
| Example 1 | PT-1 | $Pt(NO_2)_2(NH_3)_2$ | Not | 0.00 | 0.00 | 0.00 | 0.991 | 0.000 |
| Example 2 | PT-2 | $Pt(NH_3)_4Cl_2 \cdot 1.04H_2O$ | Carried | 0.05 | 0.00 | 0.00 | 0.834 | 0.000 |
| Comp. Ex. 1 | PT-3 | $Pt(NH_3)_4Cl_2 \cdot 1.04H_2O$ | Not | 0.16 | 0.00 | 0.00 | 0.779 | 0.000 |
| Comp. Ex. 2 | PT-4 | $H_2PtCl_6 \cdot 6H_2O$ | Not | 0.41 | 0.00 | 0.00 | 0.665 | 0.000 |
| Example 3 | RH-1 | $Rh(acac)_3$*2 | Not | 0.00 | 0.00 | 0.00 | 0.254 | 0.000 |
| Comp. Ex. 3 | RH-2 | $RhCl_3 \cdot 3H_2O$ | Not | 0.80 | 0.00 | 0.00 | 0.008 | 0.000 |
| Example 4 | PD-1 | $Pd(NO_3)_2$ | Not | 0.00 | 0.00 | 0.00 | 0.113 | 0.001 |
| Example 5 | PD-2 | $(CH_3COO)_2Pd$ | Not | 0.00 | 0.00 | 0.00 | 0.133 | 0.000 |
| Comp. Ex. 4 | PD-3 | $Pd(NH_3)_4Cl_2 \cdot 0.70H_2O$ | Not | 0.35 | 0.00 | 0.00 | 0.096 | 0.002 |

*1Not: not carried out  Carried: carried out
*2acac: acetylacetonate group

EXAMPLE 6

In 20 ml of distilled water, 421 mg of ammonium metavanadate and 545 mg of oxalic acid were dissolved, and 4.85 g of zirconia having a specific surface area of 104 $m^2/g$ and a particle diameter of not larger than 200 mesh, supplied by Norton Co., was then added to the solution. The mixture was dried at a reduced pressure by using a rotary evaporator and the dry product was calcined in an air stream at 400° C. for one hour to prepare 6.5% $V_2O_5$/zirconia.

With 4.0 ml of distilled water, 54 mg of a dinitrodiammineplatinum solution in nitric acid, containing 8.48% of platinum, and 107 mg of an aqueous palladium nitrate solution containing 7.71% of palladium were incorporated, and 1.00 g of the above-mentioned 6.5% $V_2O_5$/zirconia was then incorporated in the resulting solution. The mixture was dried at a reduced pressure by using a rotary evaporator and the dry product was reduced in a stream of a gaseous 10% hydrogen/90% nitrogen mixture at 250° C. for one hour to prepare a 0.50% Pt-0.82% Pd/6.5% $V_2O_5$/zirconia catalyst (hereinafter abbreviated to "Pt-Pd-1"). The X-ray fluorescent analysis revealed that chlorine, bromine and iodine were not detected in Pt-Pd-1.

A glass reactor having a 100 ml volume and equipped with a reflux condenser was charged with 20 ml of benzene and 25 ml of acetic acid, and 0.10 g of the 0.50% Pt-0.82% Pd/6.5% $V_2O_5$/zirconia catalyst (Pt-Pd-1) was added to the charge. The content of the reac- (hereinafter abbreviated to "Pt-Pd-2"). The X-ray fluorescent analysis revealed that chlorine, bromine and iodine were not detected in Pt-Pd-2.

A glass reactor having a 100 ml volume and equipped with a reflux condenser was charged with 20 ml of benzene, 25 ml of acetic acid and 6.1 mg of vanadium (III) acetylacetonate, and 0.10 g of the 0.50% Pt-0.027% Pd/zirconia catalyst (Pt-Pd-2) was added to the charge. The content of the reactor was heated to 60° C., and, while the heated content was stirred at normal pressure by a magnetic stirrer, hydrogen was supplied at a rate of 40 ml/min to the content for 30 minutes to pretreat the catalyst, and then hydrogen and air were simultaneously supplied to the content at rates of 24 ml/min and 38 ml/min, respectively, to effect oxidation of benzene. When one hour elapsed after the commencement of reaction, the product in the liquid reaction mixture was analyzed by gas chromatography. The results are shown in Table 2.

EXAMPLE 8

By the same procedure described in Example 7, a catalyst was prepared wherein 114 mg of a dinitrodiammineplatinum solution in nitric acid, containing 4.59% of platinum, and 62 mg of an aqueous palladium nitrate solution containing 4.41% of palladium were used with all other conditions remaining the same. The thus-obtained 0.50% Pt-0.27% Pd/zirconia catalyst is hereinafter abbreviated to "Pt-Pd-3". This catalyst did not contain chlorine, bromine and iodine.

Oxidation of benzene was carried out by the same procedure as that described in Example 7 except that Pt-Pd-3 was used instead of Pt-Pd-2 as the catalyst. The results are shown in Table 2.

EXAMPLE 9

By the same procedure described in Example 7, a catalyst was prepared wherein 113 mg of a dinitrodiammineplatinum solution in nitric acid, containing 4.59% of platinum, and 113 mg of an aqueous palladium nitrate solution containing 4.41% of palladium were used with all other conditions remaining the same. The thus-obtained 0.50% Pt-0.50% Pd/zirconia catalyst is hereinafter abbreviated to "Pt-Pd-4". This catalyst did not contain chlorine, bromine and iodine.

Oxidation of benzene was carried out by the same procedure as that described in Example 7 except that Pt-Pd-4 was used instead of Pt-Pd-2 as the catalyst. The results are shown in Table 2.

EXAMPLE 10

By the same procedure described in Example 7, a catalyst was prepared wherein 109 mg of a dinitrodiammineplatinum solution in nitric acid, containing 4.59% of platinum, and 185 mg of an aqueous palladium nitrate solution containing 4.41% of palladium were used with all other conditions remaining the same. The thus-obtained 0.50% Pt-0.82% Pd/zirconia catalyst is hereinafter abbreviated to "Pt-Pd-5". This catalyst did not contain chlorine, bromine and iodine.

Oxidation of benzene was carried out by the same procedure as that described in Example 7 except that Pt-Pd-5 was used instead of Pt-Pd-2 as the catalyst. The results are shown in Table 2.

EXAMPLE 11

By the same procedure described in Example 7, a catalyst was prepared wherein 40 mg of a dinitrodiammineplatinum solution in nitric acid, containing 4.59% of platinum, and 114 mg of an aqueous palladium nitrate solution containing 4.41% of palladium were used with all other conditions remaining the same. The thus-obtained 0.18% Pt-0.50% Pd/zirconia catalyst is hereinafter abbreviated to "Pt-Pd-6". This catalyst did not contain chlorine, bromine and iodine.

Oxidation of benzene was carried out by the same procedure as that described in Example 7 except that Pt-Pd-6 was used instead of Pt-Pd-2 as the catalyst. The results are shown in Table 2.

COMPARATIVE EXAMPLE 5

In 4.0 ml of distilled water, 9.0 mg of a tetraamminedichloroplatinum and 12.1 mg of tetraamminedichloropalladium were dissolved, and 1.00 g of zirconia having a specific surface area of 104 $m^2/g$ and a particle diameter of not larger than 200 mesh, supplied by Norton Co., was then added to the solution. The mixture was dried at a reduced pressure by using a rotary evaporator and the dry product was reduced in a stream of a gaseous 10% hydrogen/90% nitrogen mixture at 250° C. for one hour to prepare a 0.50% Pt-0.50% Pd/zirconia catalyst (hereinafter abbreviated to "Pt-Pd-7"). This catalyst contained 0.24% of chlorine, but did not contain bromine and iodine.

Oxidation of benzene was carried out by the same procedure as that described in Example 7 except that Pt-Pd-7 was used instead of Pt-Pd-2 as the catalyst. The results are shown in Table 2.

EXAMPLE 12

With 5.2 ml of distilled water, 109 mg of a dinitrodiammineplatinum solution in nitric acid, containing 4.59% of platinum, and 113 mg of an aqueous palladium nitrate solution containing 4.41% of palladium were incorporated, and 1.00 g of silica having a particle diameter of not larger than 200 mesh ("CARiACT-15" supplied by Fuji-Davison Co.) was then added to the resulting solution. The mixture was dried at a reduced pressure by using a rotary evaporator and the dry product was reduced in a stream of a gaseous 10% hydrogen/90% nitrogen mixture at 250° C. for one hour to prepare a 0.50% Pt-0.50% Pd/silica catalyst (hereinafter abbreviated to "Pt-Pd-8"). This catalyst did not contain chlorine, bromine and iodine.

Oxidation of benzene was carried out by the same procedure as that described in Example 7 except that Pt-Pd-8 was used instead of Pt-Pd-2 as the catalyst. The results are shown in Table 2.

EXAMPLE 13

With 18.0 ml of distilled water, 502 mg of a dinitrodiammineplatinum solution in nitric acid, containing 4.59% of platinum was incorporated, and 4.58 g of silica having a particle diameter of not larger than 200 mesh ("CARiACT-15" supplied by Fuji-Davison Co.) was then added to the resulting solution. The mixture was evaporated to dryness on a hot water bath and the dry product was reduced in a stream of a gaseous 10% hydrogen/90% nitrogen mixture at 150° C. for one hour to prepare a 0.5% Pt/silica catalyst (hereinafter abbreviated to "Pt-5"). This catalyst did not contain chlorine, bromine and iodine.

Oxidation of benzene was carried out by the same procedure as that described in Example 7 except that Pt-5 was used instead of Pt-Pd-2 as the catalyst. The results are shown in Table 2.

EXAMPLE 14

With 4.1 ml of distilled water, 108 mg of a dinitrodiammineplatinum solution in nitric acid, containing 4.59% of platinum, and 114 mg of an aqueous palladium nitrate solution containing 4.41% of palladium were incorporated, and 1.00 g of titania having a specific surface area of 118 $m^2/g$ and a particle diameter of not larger than 200 mesh, supplied by Norton Co., was then added to the resulting solution. The mixture was dried at a reduced pressure by using a rotary evaporator and the dry product was reduced in a stream of a gaseous 10% hydrogen/90% nitrogen mixture at 250° C. for one hour to prepare a 0.50% Pt-0.50% Pd/titania catalyst (hereinafter abbreviated to "Pt-Pd-9"). This catalyst did not contain chlorine, bromine and iodine.

Oxidation of benzene was carried out by the same procedure as that described in Example 7 except that Pt-Pd-9 was used instead of Pt-Pd-2 as the catalyst. The results are shown in Table 2.

EXAMPLE 15

By the same procedure as that described in Example 14, a catalyst was prepared wherein the aqueous palladium nitrate solution was not used with all other conditions remaining the same. The thus-obtained 0.50% Pt/titania catalyst is hereinafter abbreviated to "Pt-6".

This catalyst did not contain chlorine, bromine and iodine.

Oxidation of benzene was carried out by the same procedure as that described in Example 7 except that Pt-6 was used instead of Pt-Pd-2 as the catalyst. The results are shown in Table 2.

EXAMPLE 16

With 4.0 ml of distilled water, 109 mg of a dinitrodiammineplatinum solution in nitric acid, containing 4.59% of platinum, was incorporated, and 1.00 g of zirconia having a specific surface area of 104 $m^2/g$ and a particle diameter of not larger than 200 mesh, supplied by Norton Co., was then added to the resulting solution. The mixture was dried at a reduced pressure by using a rotary evaporator and the thus-obtained dry powdery product was incorporated with 5.0 g of a ruthenium (III) acetylacetonate solution in ethanol, containing 0.100% of ruthenium. The mixture was dried at a reduced pressure by using a rotary evaporator and the dry product was reduced in a stream of a gaseous 10% hydrogen/-90% nitrogen mixture at 370° C. for one hour to prepare a 0.50% Pt-0.50% Ru/zirconia catalyst (hereinafter abbreviated to "Pt-Ru-1"). This catalyst did not contain chlorine, bromine and iodine.

Oxidation of benzene was carried out by the same procedure as that described in Example 7 except that Pt-Ru-1 was used instead of Pt-Pd-2 as the catalyst. The results are shown in Table 2.

EXAMPLE 17

In 16.6 ml of $2.2 \times 10^{-4}$ N hydrochloric acid, 8.5 mg of iridium chloride was dissolved, and the resulting solution was incorporated with 113 mg of a dinitrodiammineplatinum solution in nitric acid, containing 4.59% of platinum. The mixed solution was incorporated with 1.00 g of zirconia having a specific surface area of 104 $m^2/g$ and a particle diameter of not larger than 200 mesh, supplied by Norton Co. The mixture was dried at a reduced pressure by using a rotary evaporator and the dried product was reduced in a stream of a gaseous 10% hydrogen/90% nitrogen mixture at 270° C. for one hour to prepare a 0.50% Pt-0.50% Ir/-zirconia catalyst (hereinafter abbreviated to "Pt-Ir-1"). This catalyst contained 0.05% of chlorine but did not contain bromine and iodine.

Oxidation of benzene was carried out by the same procedure as that described in Example 7 except that Pt-Ir-1 was used instead of Pt-Pd-2 as the catalyst. The results are shown in Table 2.

EXAMPLE 18

With 8.0 ml of distilled water, 218 mg of a dinitrodiammineplatinum solution in nitric acid, containing 4.59% of platinum, was incorporated, and 2.00 g of zirconia having a specific surface area of 104 $m^2/g$ and a particle diameter of not larger than 200 mesh, supplied by Norton Co., was then added to the resulting solution. The mixture was dried at a reduced pressure by using á rotary evaporator. A portion (1.00 g) of the thus-obtained dry powdery product was incorporated with 6.3 g of a rhodium (III) acetylacetonate solution in ethanol, containing 0.081% of rhodium. The mixture was dried at a reduced pressure by using a rotary evaporator and the dry product was reduced in a stream of a gaseous 10% hydrogen/90% nitrogen mixture at 350° C. for one hour to prepare a 0.50% Pt-0.50% Rh/zirconia catalyst (hereinafter abbreviated to "Pt-Rh-1"). This catalyst did not contain chlorine, bromine and iodine.

Oxidation of benzene was carried out by the same procedure as that described in Example 7 except that Pt-Rh-1 was used instead of Pt-Pd-2 as the catalyst. The results are shown in Table 2.

TABLE 2

| Example No. | Catalyst | | | | | Halogen content (% by weight) | | | Rate of production (m-mol/hr) | |
|---|---|---|---|---|---|---|---|---|---|---|
| | Amount of Pt (wt. %) | Amount of Pd (wt. %) | Amount of other metal (wt. %) | Pd/Pt or M/Pt*1 | Carrier | Cl | Br | I | Phenol | Benzoquinone |
| Example 6 | 0.50 | 0.82 | — | 3.0 | $V_2O_5$/Zirconia | 0.00 | 0.00 | 0.00 | 1.28 | 0.025 |
| Example 7 | 0.50 | 0.027 | — | 0.1 | Zirconia | 0.00 | 0.00 | 0.00 | 0.971 | 0.000 |
| Example 8 | 0.50 | 0.27 | — | 1.0 | Zirconia | 0.00 | 0.00 | 0.00 | 1.40 | 0.003 |
| Example 9 | 0.50 | 0.50 | — | 1.8 | Zirconia | 0.00 | 0.00 | 0.00 | 1.56 | 0.010 |
| Example 10 | 0.50 | 0.82 | — | 3.0 | Zirconia | 0.00 | 0.00 | 0.00 | 1.44 | 0.023 |
| Example 11 | 0.18 | 0.50 | — | 5.0 | Zirconia | 0.00 | 0.00 | 0.00 | 1.19 | 0.012 |
| Comp. Ex. 5 | 0.50 | 0.50 | — | 1.8 | Zirconia | 0.24 | 0.00 | 0.00 | 1.08 | 0.012 |
| Example 12 | 0.50 | 0.50 | — | 1.8 | Silica | 0.00 | 0.00 | 0.00 | 1.23 | 0.002 |
| Example 13 | 0.50 | — | — | 0 | Silica | 0.00 | 0.00 | 0.00 | 0.753 | 0.000 |
| Example 14 | 0.50 | 0.50 | — | 1.8 | Titania | 0.00 | 0.00 | 0.00 | 1.44 | 0.129 |
| Example 15 | 0.50 | — | — | 0 | Titania | 0.00 | 0.00 | 0.00 | 0.698 | 0.006 |
| Example 16 | 0.50 | — | Ru 0.50 | 1.9 | Zirconia | 0.00 | 0.00 | 0.00 | 0.855 | 0.001 |
| Example 17 | 0.50 | — | Ir 0.50 | 1.0 | Zirconia | 0.05 | 0.00 | 0.00 | 0.789 | 0.001 |
| Example 18 | 0.50 | — | Rh 0.50 | 1.9 | Zirconia | 0.00 | 0.00 | 0.00 | 0.654 | 0.000 |

*1 Atomic ratio of Pd/Pt or other metal/Pt

EXAMPLE 19

In 20 ml of distilled water, 45.5 mg of tetraamminedichloroplatinum was dissolved, and 5.00 g of silica having a particle diameter of 10 to 20 mesh ("CARiACT-15" supplied by Fuji-Davison Co.) was then added to the resulting solution. The mixture was evaporated to dryness on a hot water bath and the dry product was reduced in a stream of a gaseous 10% hydrogen/90% nitrogen mixture at 150° C. for two hours to prepare a 0.5% Pt/silica catalyst. This catalyst contained 0.15% of chlorine, but did not contain bromine and iodine.

A glass tubular reactor having an inner diameter of 8 mm was charged with 1.50 g of the 0.5% Pt/silica catalyst. Oxidation of benzene was carried out at 60° C. while (i) a mixed solution of 40% benzene/60% acetic acid having dissolved therein 3.4 ppm (as vanadium metal) of vanadium (III) acetylacetonate and 6.68 ppm of acetylacetone, (ii) hydrogen and (iii) air were simultaneously supplied to the reactor at rates of 0.25 ml/min, 24 ml/min and 38 ml/min, respectively. The product was analyzed by the gas chromatography. The results are shown in Table 3.

EXAMPLE 20

Oxidation of benzene was carried out by the same procedure as described in Example 19 wherein acetylacetone was not used with all other conditions remaining the same. The results are shown in Table 3.

As shown in Tables 1, 2 and 3, according to the process of the present invention, oxidation of an aromatic compound is effectively carried out, namely, a phenol can be yielded with a high selectivity and a high catalytic activity can be maintained for a long reaction time.

TABLE 3

| Acetylacetone | Example 19 Used | | Example 20 Not used | |
|---|---|---|---|---|
| Time elapsed from commencement of reaction (hours) | Rate of production (m-mol/hr) | | | |
| | Phenol | Benzoquinone | Phenol | Benzoquinone |
| 5 | 0.131 | 0.000 | 0.109 | 0.000 |
| 10 | 0.121 | 0.000 | 0.105 | 0.000 |
| 30 | 0.112 | 0.000 | 0.092 | 0.000 |
| 80 | 0.109 | 0.000 | 0.074 | 0.000 |
| 150 | 0.096 | 0.000 | 0.071 | 0.000 |
| 250 | 0.096 | 0.000 | 0.070 | 0.000 |
| 280 | 0.093 | 0.000 | 0.057 | 0.000 |
| 300 | 0.092 | 0.000 | 0.056 | 0.000 |
| 350 | 0.093 | 0.000 | 0.059 | 0.000 |
| 380 | 0.090 | 0.000 | 0.040 | 0.000 |
| 400 | 0.089 | 0.000 | — | — |
| 450 | 0.095 | 0.000 | — | — |
| 500 | 0.086 | 0.000 | — | — |

EXAMPLES 21, 22 AND 23

Oxidation of toluene, diphenyl and naphthalene was carried out by the same procedure as that described in Example 7 except that Pt-Pd-4 prepared in Example 9 was used instead of Pt-Pd-2 as the catalyst and toluene, diphenyl and naphthalene were used, respectively, instead of benzene. The results are shown in Table 4.

TABLE 4

| | Starting material and amount (ml) | | Rate of production (m-mol/hr) |
|---|---|---|---|
| Example 21 | Toluene | 20 ml | 1.35*1 |
| Example 22 | Diphenyl | 20 ml | 0.64*2 |
| Example 23 | Naphthalene | 22 ml | 0.55*3 |

*1 The rate of production is based on the total amount of o-, m- and p-cresols. In this process, a minor amount of benzyl alcohol was also produced.
*2 The rate of production is based on the total amount of 2-, 3- and 4-hydroxydiphenyls. A minor amount of dihydroxydiphenyls was also produced.
*3 The rate of production was based on the total amount of α- and β-hydroxynaphthalene.

What is claimed is:

1. An improvement in a process for producing a phenol which comprises reacting an aromatic compound with oxygen and hydrogen in the liquid phase in the presence of a catalyst comprising a noble metal of group VIII of the periodic table, which is supported on a carrier, and in the co-presence of a vanadium compound, said improvement comprising using as the catalyst a catalyst containing not more than 0.15% by weight, based on the weight of the catalyst, of halogens.

2. The process for producing a phenol as claimed in claim 1, wherein the noble metal of group VIII of the periodic table is at least one noble metal selected from the group consisting of ruthenium, rhodium, palladium, iridium and platinum.

3. The process for producing a phenol as claimed in claim 1, wherein the noble metal of group VIII of the periodic table consists of both platinum and palladium.

4. The process for producing a phenol as claimed in claim 1, wherein the vanadium compound is at least one vanadium compound selected from the group consisting of vanadium (III) acetylacetonate and vanadium oxide acetylacetonate.

5. The process for producing a phenol as claimed in claim 1, wherein the vanadium compound and the catalyst are separately incorporated in the reaction system.

6. The process for producing a phenol as claimed in claim 5, wherein the vanadium compound is at least one vanadium compound selected from the group consisting of vanadium (III) acetylacetonate and vanadium oxide acetylacetonate.

7. The process for producing a phenol as claimed in claim 1, wherein the vanadium compound is vanadium pentoxide.

8. The process for producing a phenol as claimed in claim 1, wherein the vanadium compound is supported on the carrier in the reaction system.

9. The process for producing a phenol as claimed in claim 8, wherein the vanadium compound is vanadium pentoxide.

10. An improvement in a process for producing a phenol which comprises reacting an aromatic compound with oxygen and hydrogen in the liquid phase in the presence of a catalyst comprising a noble metal of group VIII of the periodic table, which is supported on a carrier, and in the co-presence of a vanadium compound, said improvement comprising carrying out the reaction further in the co-presence of a diketone compound represented by the following formula (1) or formula (2):

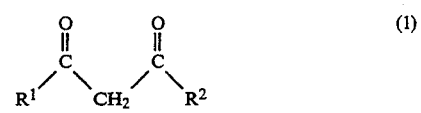

wherein $R^1$ and $R^2$ independently represents an aryl group having 6 to 10 carbon atoms or an alkyl group having 1 to 8 carbon atoms, which groups may have a substituent,

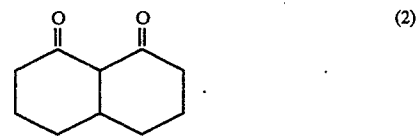

11. The process for producing a phenol as claimed in claim 10, wherein the noble metal of group VIII of the periodic table is at least one noble metal selected from the group consisting of ruthenium, rhodium, palladium, iridium and platinum.

12. The process for producing a phenol as claimed in claim 10, wherein the noble metal of group VIII of the periodic table consists of both platinum and palladium.

13. The process for producing a phenol as claimed in claim 10, wherein the vanadium compound is at least one vanadium compound selected from the group consisting of vanadium (III) acetylacetonate and vanadium oxide acetylacetonate.

14. The process for producing a phenol as claimed in claim 10, wherein the vanadium compound and the catalyst are separately incorporated in the reaction system.

15. The process for producing a phenol as claimed in claim 14, wherein the vanadium compound is at least one vanadium compound selected from the group consisting of vanadium (III) acetylacetonate and vanadium oxide acetylacetonate.

16. The process for producing a phenol as claimed in claim 10, wherein the vanadium compound is vanadium pentoxide.

17. The process for producing a phenol as claimed in claim 10, wherein the vanadium compound is supported on the carrier in the reaction system.

18. The process for producing a phenol as claimed in claim 17, wherein the vanadium compound is vanadium pentoxide.

19. The process for producing a phenol as claimed in claim 10, wherein the diketone compound is at least one diketone compound selected from the group consisting of acetylacetone, propionylacetone, butyrylacetone, isobutyrylacetone, caproylacetone, trifluoroacetylacetone, thenoyltrifluoroacetone, benzoylacetone, dibenzoylmethane and decalin-1,8-dion.

20. The process for producing a phenol as claimed in claim 10, wherein the amount of the diketone compound is from 0.01 to 1.5 equivalent per gram atom of vanadium.

21. The process for producing a phenol as claimed in claim 10, wherein the amount of the content of halogens in the catalyst supported by the carrier is not larger than 0.15% by weight based on the weight of the catalyst.

* * * * *

UNITED STATES PATENT AND TRADEMARK OFFICE
CERTIFICATE OF CORRECTION

PATENT NO. : 5,426,245
DATED : June 20, 1995
INVENTOR(S) : Hamada et al

It is certified that error appears in the above-indentified patent and that said Letters Patent is hereby corrected as shown below:

On the Title page;

item [75] Inventors, correct spelling of first inventor's city residence from "Shinanyo" to --Shinnanyo--.

item [30] Foreign Application Priority Data, change number of last priority data from "5-79356" to --5-279356--.

Column 9, line 19, delete "fitered" and replace by --filtered--.

Signed and Sealed this

Tenth Day of October, 1995

Attest:

BRUCE LEHMAN

*Attesting Officer*      *Commissioner of Patents and Trademarks*